US009744247B2

(12) United States Patent
Ventosa Rull et al.

(10) Patent No.: US 9,744,247 B2
(45) Date of Patent: Aug. 29, 2017

(54) FUNCTIONALIZED LIPOSOMES USEFUL FOR THE DELIVERY OF BIOACTIVE COMPOUNDS

(71) Applicants: CONSEJO SUPERIOR DE INVESTIGACIONES CIENTÍFICAS (CSIC), Madrid (ES); FUNDACIÓ PARC CIENTÍFIC DE BARCELONA, Barcelona (ES); CENTRO DE INVESTIGACIÓN BIOMÉDICA EN RED, Madrid (ES); FUNDACIÓ INSTITUT DE RECERCA BIOMÈDICA (IRB BARCELONA), Barcelona (ES); UNIVERSITAT DE BARCELONA, Barcelona (ES); FUNDACIÓ HOSPITAL UNIVERSITARI VALL D'HEBRON-INSTITUT DE RECERCA, Barcelona (ES); UNIVERSITAT AUTÒNOMA DE BARCELONA, Bellaterra (ES)

(72) Inventors: Leonor Ventosa Rull, Barcelona (ES); Jaume Veciana Miró, Barcelona (ES); Ingrid Cabrera Puig, Sabadell (ES); Elisa Elizondo Saez De Vicuña, Barcelona (ES); Marta Melgarejo Diaz, Badalona (ES); Miriam Royo Expósito, Barcelona (ES); Fernando Albericio Palomera, Barcelona (ES); Daniel Pulido Martinez, Viladecans (ES); Santiago Sala Vergés, Vic (ES); Jose Luis Corchero Nieto, Granollers (ES); Simón Schwartz Navarro, Cardedeu (ES); Ibane Abasolo Olaortua, Barcelona (ES); Antonio Pedro Villaverde Corrales, El Masnou (ES)

(73) Assignees: CONSEJO SUPERIOR DE INVESTIGACIONES CIENTÍFICAS (CSIC), Madrid (ES); FUNDACIÓ PARC CIENTÍFIC DE BARCELONA, Barcelona (ES); CENTRO DE INVESTIGACIÓN BIOMÉDICA EN RED, Madrid (ES); FUNDACIÓ INSTITUT DE RECERCA BIOMÈDICA (IRB BARCELONA), Barcelona (ES); UNIVERSITAT DE BARCELONA, Barcelona (ES); FUNDACIÓ HOSPITAL UNIVERSITARI VALL D'HEBRON—INSTITUT DE RECERCA, Barcelona (ES); UNIVERSITAT AUTÒNOMA DE BARCELONA, Bellaterra (ES)

(*) Notice: Subject to any disclaimer, the term of this patent is extended or adjusted under 35 U.S.C. 154(b) by 0 days.

(21) Appl. No.: 14/411,097

(22) PCT Filed: Jun. 28, 2013

(86) PCT No.: PCT/EP2013/063646
§ 371 (c)(1),
(2) Date: Dec. 23, 2014

(87) PCT Pub. No.: WO2014/001509
PCT Pub. Date: Jan. 3, 2014

(65) Prior Publication Data
US 2015/0190530 A1 Jul. 9, 2015

(30) Foreign Application Priority Data
Jun. 29, 2012 (ES) .................................. 201231020

(51) Int. Cl.
A61K 38/00 (2006.01)
A61K 47/48 (2006.01)
A61K 38/47 (2006.01)

(52) U.S. Cl.
CPC ........ A61K 47/48815 (2013.01); A61K 38/47 (2013.01); A61K 47/48123 (2013.01); A61K 47/48215 (2013.01); A61K 47/48246 (2013.01); A61K 47/48292 (2013.01); C12Y 302/01022 (2013.01); Y10T 428/2982 (2015.01)

(58) Field of Classification Search
None
See application file for complete search history.

(56) References Cited

FOREIGN PATENT DOCUMENTS

FR 2854896 A1 11/2004

OTHER PUBLICATIONS

Gelhausen et al. Colloids Surfaces B. Biointerfaces 10 (1998) 395-404.*
Gelhausen (Colloids and Surfaces B: Biointerfaces 10 (1998) 395-404.*
Jiang et al. Chinese Chemical Letters 19, 2008, 127-129.*
Lei et al. Chinese Chemical Letters 22, 2011, 831-834.*
International Search Report and Written Opinion Issued Aug. 7, 2013 in PCT/EP2013/063646, 13 pgs.
Berrow et al., "A versatile ligation-independent cloning method suitable for high-throughput expression screening applications", Nucleic Acids Res vol. 35, No. 6, e45, 12 pgs. (2007).
Boomer et al., "Cytoplasmic delivery of liposomal contents mediated by an acid-labile cholesterol-vinyl Ether-PEG conjugate", Bioconj. Chem. vol. 20, pp. 47-59 (2009).

(Continued)

Primary Examiner — Jeanette Lieb
(74) Attorney, Agent, or Firm — Squire Patton Boggs (US) LLP

(57) ABSTRACT

The invention relates to conjugates in which a sterol is functionalized by an ether bond with a water-soluble polymer to which a guiding ligand is bound. These conjugates improve the physico-chemical and delivery properties of their carrying vesicles, making these more stable, homogeneous and effective. A method for their preparation, a pharmaceutical composition containing said liposomes, and their therapeutic use are described as well.

19 Claims, 6 Drawing Sheets

(56) References Cited

OTHER PUBLICATIONS

Cano-Sarabia et al., "Preparation of Uniform Rich Cholesterol Unilamellar Nanovesicles Using $CO_2$-Expanded Solvents", Langmuir vol. 24, pp. 2433-2437 (2008).

Corchero et al., "Integrated approach to produce a recombinant, his-tagged human α-galactosidase A in mammalian cells", Biotechnol Prog. vol. 27, pp. 1206-1217 (2011).

Dai et. al., "An improved synthesis of a selective $\alpha_v\beta_3$-integrin antagonist cyclo (-RGDfK-)", Tetrahedron Letters, vol. 41, pp. 6295-6298 (2000).

Desnick et al., "Fabry's disease: enzymatic diagnosis of hemizygotes and heterozygotes, galactosidase activities in plasma, serum, urine, and leukocytes", J. Lab. and Clin. Med. vol. 81, pp. 157-171 (1973).

Dubey et al., "Liposomes modified with cyclic RGD peptide for tumor targeting", J. Drug Targ., vol. 12 (5), pp. 257-264 (2004).

Gelhausen et al., "Lectin recognition of liposomes containing neoglycolipids. Influence of their lipidic anchor and spacer length", Colloids and Surfaces B: Biointerfaces, vol. 10, pp. 395-404 (1998).

Jiang et al.,"Synthesis of a novel multivalent galactoside with high hepatocyte targeting for gene delivery", Chinese Chemical Lett. vol. 19, pp. 127-129 (2008).

Lei et al., "Design, synthesis and preliminary bio-evaluation of glucose-cholesterol derivatives as ligands for brain targeting liposomes", Chinese Chemical Lett. vol. 22, pp. 831-834 (2011).

Mayes et al., "Differential assay for lysosomal alpha-galactosidases in human tissues and its application to Fabry's disease", Clin. Chim. Acta vol. 112, pp. 247-251 (1981).

Negishi et al., "Preparation and characterization of laminin-derived peptide AG73-coated liposomes as a selective gene delivery tool", Biol. Pharm. Bull., vol. 33 (10), pp. 1766-1769 (2010).

Pan et al., "Synthesis of cetuximab-immunoliposomes via a cholesterol-based membrane anchor for targeting of EGFR", Bioconjugate Chem., vol. 18, pp. 101-108 (2007).

Shu et al., "An in vitro model of Fabry disease", J. Am. Soc. Nephrol. vol. 16, pp. 2636-2645 (2005).

Thomson et al., "Neutral postgrafted colloidal particles for gene delivery", Bioconj. Chem. vol. 16, pp. 608-614 (2005).

Torchilin "Recent advances with liposomes as pharmaceutical carriers", Nature Rev. Drug Disc. vol. 4, pp. 145-160 (2005).

Yonenaga et al., "RGD-based active targeting of novel polycation liposomes bearing siRNA for cancer treatment", J. Controlled Release vol. 160, pp. 177-181 (2012).

Ziegler et al., "Correction of the nonlinear dose response improves the viability of adenoviral vectors for gene therapy of Fabry Disease", Human Gene Therapy vol. 13, pp. 935-945 (2002).

\* cited by examiner

FUNCTIONALIZED LIPOSOMES USEFUL FOR THE DELIVERY OF BIOACTIVE COMPOUNDS

CROSS-REFERENCE TO RELATED APPLICATIONS

This application is the National Stage of International Patent Application No. PCT/EP2013/063646, filed Jun. 28, 2013, which claims the benefit of ES Application No. P 201231020, filed Jun. 29, 2012, each of which is incorporated by reference in its entirety.

The present invention is related to new functionalized liposomes for the selective delivery of active agents. These liposomes, due to their functionalization with multiple guiding ligands, may have potential applications in cosmetics and therapy.

BACKGROUND ART

Liposomes are vesicles comprising a lipid bilayer similar to that of the cell. In their interior there is an aqueous solution in which different molecules such as natural products, synthetic drugs or nucleic acid can be found. These vesicles are currently used as carriers and molecular delivery systems with many different applications. Typical applications include delivery of bioactive compounds in therapy or cosmetics.

Liposomes are constantly evolving, and some of the problems associated with their use in a first generation, as for example a short plasma half-life or a non-specific binding, have been partly solved (Torchilin V. "Recent advances with liposomes as pharmaceutical carriers". *Nature Rev. Drug Disc.* 2005, vol. 4, pp. 145-160). With the aim of reducing the rapid elimination of liposomes in the circulation, they have been coated with soluble, inert and biocompatible polymers such as e.g. polyethylene glycol (PEG), which forms a protective layer that slows down the recognition by opsonins, thus increasing their bioavailability. As for the non-specific binding, which could cause the incorrect delivery of their contents, an increasing number of functionalized ligands on the surface of the liposomes have been tested, in an attempt to transform them into specific delivery systems. These targeting molecules can range from small molecules such as folate or biotin, to peptides or even antibodies.

Liposomes simultaneously functionalized with coating polymers and a guiding ligand, with the goal of trying to achieve a longer half-life and at the same time a more efficient and selective delivery of its content, have also been described. Thus, for example, liposomes have been described where one of membrane phospholipids (distearoylphosphatidylethanolamine, or DSPE) has been used as an anchor for the covalent binding of a chain of polyethylene glycol (PEG) which, in turn, has been used to covalently anchor a guiding ligand, in this case, a cyclic RGD peptide (Dubey P., et. al. "Liposomes modified with cyclic RGD peptide for tumor targeting". *J. Drug Targ.* 2004, vol. 12, pp. 257-264). In the state of the art, other references disclosing liposomes with conjugates of the type phospholipid-PEG-[guiding ligand] are found. For example, liposomes with conjugates of the type DSPE-PEG-AG73 (Negishi Y., et. al. "Preparation and characterization of laminin-derived peptide AG73-coated liposomes as a selective gene delivery tool". *Biol. Pharm. Bull.* 2010, vol. 33, pp. 1766-1769) have been described. AG73 is a peptide derived from the globular domain of the α1 chain of laminin, which is known to bind to syndecan-2, a receptor overexpressed in some cancers.

Although phospholipids have been used as anchoring points, other constituents of the liposomes have been explored, especially cholesterol. Thus, for example, references that describe conjugates of the type cholesterol-PEG-[guiding ligand] are found. A conjugate of cholesterol-PEG-Cetuximab has been described for the delivery of boron compounds on cancerous cells which overexpress the Cetuximab receptor, EGFR (Pan X., et. al. "Synthesis of cetuximab-immunoliposomes via a cholesterol-based membrane anchor for targeting of EGFR". *Bioconjugate Chem.* 2007, vol. 18, pp. 101-108). Another example of the state of the art is the conjugate of the type cholesterol-PEG-RGD for the selective delivery of coding DNA in gene therapy on cells overexpressing integrin αvβ3 (Thomson B., et. al. "Neutral postgrafted colloidal particles for gene delivery". *Bioconj. Chem.* 2005, vol. 16, pp. 608-614).

It should be noted that the covalent bonding between the cholesterol of the liposome membrane and the tandem PEG-[guiding ligand] in all of these references is achieved by an ester- or carbamate-type bond.

On the other hand, liposomes which have been functionalized with other groups have been described. In particular, there have been described functionalized liposomes with conjugates in which the cholesterol is bound to the PEG through a vinyl ether (called CVEP) (Boomer J., et. al. "Cytoplasmic delivery of liposomal contents mediated by an acid-labile cholesterol-vinyl ether-PEG conjugate" *Bioconj. Chem.* 2009, vol. 20, 47-69). The vinyl ether group is cleaved in an acidic medium, resulting in the loss of the PEG coating. These liposomes additionally contain a second conjugate of DSPE-PEG-folate that directs them to cells overexpressing the folate receptor.

Although some technical problems associated with the use of liposomes have been partially resolved, there is still a need for conjugates that confer better physico-chemical, and pharmacological properties to the carrying liposomes.

DESCRIPTION OF THE INVENTION

The present invention is related to liposomes carrying a conjugate based on functionalizing a sterol present in its lipid bilayer with a chain of polyethylene glycol which, in turn, is functionalized with a guiding ligand. The binding between the cholesterol molecule and the PEG is made by an alkyl ether group, in contrast to those of the state of the art which use other chemical groups, such as carbamate. This new covalent bonding confers to the liposomes carrying the conjugates, improved physico-chemical and delivery properties. In particular, inventors have found that liposomes carrying conjugates with an ether bond demonstrate a superior suspension stability than the liposomes carrying conjugates with a carbamate bond. That is, the conjugates with the ether bond have a slower sedimentation rate than those where the cholesterol and the chain of PEG are bound by a carbamate. This entails that liposomes with conjugates of the present invention are more stable in suspension than those described in the state of the art. It should be noted that there are no references in the state of the art which suggest that this ether-type covalent bonding can confer said suspension stability.

On the other hand, the inventors have surprisingly found that the conjugates of the type cholesterol-(ether)-PEG-[guiding ligand] confer the liposomes a more homogeneous particle size than that conferred by the conjugates of the type cholesterol-(carbamate)-PEG-[guiding ligand]. The latter, demonstrate a bimodal particle-size distribution, while those of the invention have a more homogeneous, monomodal distribution.

The physico-chemical properties of homogeneity and lower sedimentation rate of the liposomes carrying the conjugates of the invention can be an advantage in the production, handling and use of liposomes functionalized with therapeutic agents.

Additionally, it has also been surprisingly found that the liposomes carrying the conjugates of the invention have improved properties in the delivery of their contents. Thus, liposomes bearing conjugates with an ether bond connecting the cholesterol and the PEG have superior delivery of their contents to the target cells than liposomes bearing conjugates with a carbamate bond connecting the cholesterol and the PEG.

Thus, a first aspect of the present invention is to provide a conjugate comprising: i) a sterol; ii) a chain of polyethylene glycol having a proximal end and a distal end where said chain of polyethylene glycol is covalently bound by its proximal end to i) via a bond of the type alkyl ether; iii) a guiding ligand, capable of selectively binding to one or several receptors present in a target cell, said guiding ligand being covalently bound to the distal end of ii).

In a preferred embodiment, the conjugate of the present invention is one in which the sterol is cholesterol.

In another preferred embodiment, the conjugate is one in which the chain of polyethylene glycol has a number of repetitions from 1 to 30. In another more preferred embodiment, the chain of polyethylene glycol has a number of repetitions from 2 to 10.

In another preferred embodiment, the conjugate is one in which the guiding ligand is a peptide. In another more preferred embodiment, the guiding ligand comprises the RGD sequence. In another still more preferred embodiment, the guiding ligand is a peptide with the sequence SEQ ID NO: 1: RGDFK, wherein the RGD and K residues are L-amino acids and the F residue is a D-amino acid.

The RGD peptides are peptides commonly described in the art as peptides that are able to interact with integrins present in the membrane of various cell lines, and of particular interest for the study of cell adhesion, both between cells and between cells and different tissues or the basement membrane. The RGD peptide used the examples described, in both the conjugate which is part of the invention (ether bond) and the closest state of the art (carbamate bond), is a peptide with RGDfK sequence, wherein the phenylalanine is the only D-amino acid (this is why it has been distinguished in the sequence with a lowercase letter), and wherein the covalent bond with the polyethylene glycol has been carried out functionalizing the lysine side-chain.

A second aspect of the present invention is a liposome comprising a conjugate as defined above.

In a preferred embodiment, the liposome as defined above has a monomodal particle size distribution.

In another preferred embodiment, the liposome as defined above has an average particle size from 25 up to 500 nanometer, and the average Z potential in absolute value is from 20 up to 90 mV.

In another preferred embodiment, the liposome as defined above further comprises a therapeutic agent. In a more preferred embodiment, the therapeutic agent is the α-galactosidase (or GLA for short).

A third aspect of the present invention is the use of the liposome defined above as a delivery system of therapeutic agents.

A fourth aspect of the present invention is related to the liposomes defined above for use as a medicament.

A fifth aspect of the invention is related to the use of the liposome comprising the therapeutic agent α-galactosidase for the preparation of a medicament for the prevention and/or treatment of Fabry disease.

This preferred embodiment can be reformulated as a liposome comprising the therapeutic agent α-galactosidase for use in the treatment and/or prevention of Fabry disease.

It is also considered part of the invention a method for the treatment and/or prevention of the Fabry disease, comprising administering a therapeutically effective amount of the liposomes as defined above, together with pharmaceutically acceptable excipients or carriers, in a subject in need of such treatment, including a human.

A sixth aspect of the present invention is a pharmaceutical composition comprising a therapeutically effective amount of the liposomes defined above together with pharmaceutically acceptable excipients and/or carriers.

A seventh aspect of the present invention is to provide a method for the preparation of the conjugate as defined above comprising the following steps: a) reacting a sterol with a sulfonyl halide in the presence of a base and a solvent to give the corresponding sulfonyl ester; b) reacting the compound obtained in the step a) with a polyethylene glycol with a number of repetitions from 2 a 10 in the presence of a solvent; c) activating the compound obtained in the step b) with disuccinimidyl carbonate; d) reacting the compound resulting from the step c) with a peptide comprising the RGD sequence in the presence of a base and a solvent. Preferably, the sulfonyl ester is a mesylate, besylate, or tosylate.

An eighth aspect of the present invention is to provide a method for the preparation of liposomes as defined above comprising the following steps:
a) Preparing an aqueous solution which may optionally include a surfactant;
b) Preparing a solution comprising the conjugate as defined above, cholesterol and, optionally, a phospholipid dissolved in an organic solvent, where the organic solution is expanded with a compressed fluid;
c) Optionally, adding a therapeutic agent either to the solution of the step a), or to the solution of the step b) before expanding this solution; and d) Depressurizing the solution resulting from the step b) over the resulting solution of the step a). Preferably the surfactants are salts of ternary amine, quaternary ammonium salt and alkyl-ammoniums in saturated and unsaturated heterocycles. In addition, preferably the compressed fluids are carbon dioxide ($CO_2$), ethane, propane, the hydrochlorofluorocarbons (for example, CFC-22) and hydrofluorocarbons (for example, HFC-134A).

Throughout the description and claims, the word "comprises" and its variations are not intended to exclude other technical features, additives, components or steps. Furthermore, the word "comprise" encompasses the case of "consisting of". For those skilled in the art, other objects, advantages and characteristics of the invention will emerge in part from the description and in part from the practice of the invention. The following examples and drawings are provided by way of illustration, and are not intended to be limiting of the present invention. Furthermore, the present invention covers all the possible combinations of particular and preferred embodiments herein indicated.

Definitions

The terms "liposome" and "vesicle" as used herein, are interchangeable. For the person skilled in the art, it is normally understood that a vesicle which is called liposome has some phospholipid present in its membrane, whereas the term vesicle is also used when the liposome lacks phospholipids. In any case, the conjugates which are part of the invention may be included in vesicles containing or lacking phospholipids.

The term "alpha-galactosidase" (GLA for short) as used herein, refers to the glycoside hydrolase enzyme that hydrolyses the terminal alpha-galactosyl moieties from glycolipids and glycoproteins. It is encoded by the GLA gene. It predominantly hydrolyzes ceramide trihexoside, and it can catalyze the hydrolysis of melibiose into galactose and glucose. As it is here understood, GLA can mean an alpha-galactosidase cloned and expressed both in procariotes and eucariotes, a truncated GLA enzyme, or GLA derivatives that still retain its original catalytic activity.

The term "therapeutic agent" as used herein, refers to any kind of substance, molecule or mixture of substances or molecules which are to be administered in order to have a beneficial effect and which is encapsulated, trapped or complexed in the liposome.

The term "therapeutically effective amount" as used herein, refers to an amount of a compound which, when administered, is enough to prevent the development of, or alleviate in some way, one or more symptoms of a disease or condition. The particular dose of compound administered according to the invention will be set obviously by the circumstances associated with each case, including the administered compound, the route of administration, the disease being treated, and similar considerations.

The term "pharmaceutical composition" refers to the mixture of vesicles which are disclosed here with other chemical components, e.g. solvents. The pharmaceutical composition facilitates the administration of vesicles which carry the therapeutic agent to the organism.

The term "pharmaceutically acceptable excipient" refers to a pharmaceutically acceptable material, composition or vehicle, such as for example a liquid or solid filling, excipient, solvent, or encapsulation material. Each component has to be pharmaceutically acceptable in the sense of being compatible with other ingredients of the pharmaceutical composition. It has to be suitable for use in contact with tissues or organs of humans and animals without too much toxicity, irritation or allergic response, immunogenicity or other problems or complications with a reasonable risk/benefit ratio.

The term "treatment" as used herein, refers to alleviate or eradicate a disease or condition, alleviate or eradicate one or more symptoms associated with the disease or condition, or to alleviate or eradicate the cause of the disease or condition.

EXAMPLES

Example 1. Preparation of Conjugates

Figure 1:
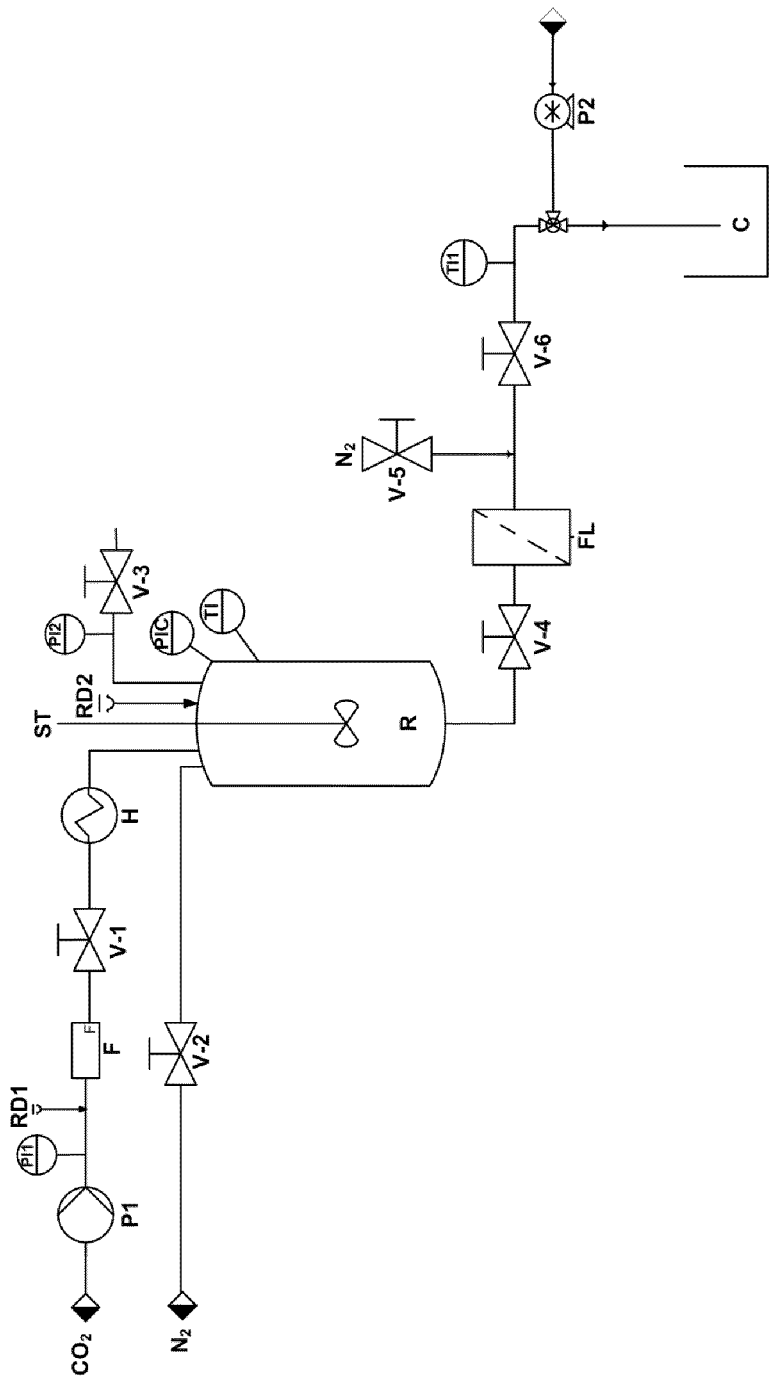
FIG. 1. Assembly illustrating the method for the preparation of vesicles of the invention (Abbreviations: R: High-pressure vessel; V: Valve; P: Pump; F: Flow-meter; H: Heat-exchanger; ST: Stirrer; FL: Filter; TI: Temperature Indicator; PIC: Pressure indicator and Controller; C: Collector; RD: Rupture Disc)

Conjugates which form part of the invention (with ether bond between the cholesterol and the PEG), and those which have been described in the state of the art (with carbamate bond between the cholesterol and the PEG) were synthesized with the steps detailed below. Acronyms used in the experimental summary are:
ACN: Acetonitrile.
CDI: 1,1'-Carbonyldiimidazole
DCM: Dichloromethane
DIPEA: N,N-Diisopropylethylamine
DMF: N,N-Dimethylformamide
DSC: Disuccinimidyl carbonate
HPLC-MS: High Performance Liquid Chromatography-Mass Spectrometry
HPLC-PDA: High Performance Liquid Chromatography-Mass Spectrometry-Photodiode Array Detector
NMR: Nuclear Magnetic Resonance
TMBE: Methyl tert-butyl ether
TFA: Trifluoroacetic acid
TIS: Triisopropylsilane

Example 1a: Preparation of Conjugates with Ether Bond

Preparation of Cholesterol Tosyl (A)

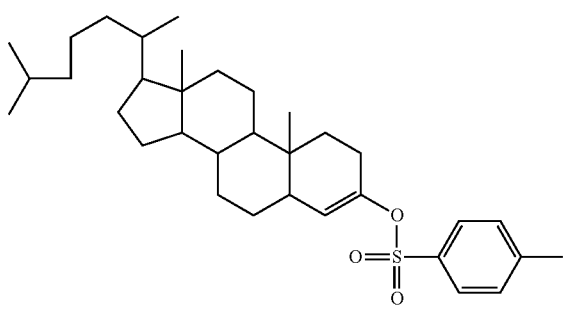

(A)

Into a flask, the cholesterol (1 eq., 1.006 g) was introduced, dissolved in anhydrous pyridine (12 mL). Tosyl chloride (2 eq., 1.004 g) was then added and the solution was left under stirring for 24 h at room temperature. Over the solution were added 5 mL of water and the crude was extracted with DCM (3×6 mL). Et$_2$O (total solution) was added in the organic phase and then dried over MgSO$_4$, filtered and the solvent was removed to dryness. The crude was recrystallized from petroleum ether, obtaining a white solid (0.969 g, 70%).

HPLC-PDA: (C18, 5-100% B, A: ACN B: MeOH, 4.5 min, 2 mL/min, λ=210 nm) r$_T$: 2.7 min (89%) $^1$H NMR: (400 MHz, CDCl$_3$) δ: 0.65 (s, 3H); 0.85 (d, 1.6 Hz, 3H); 0.87 (d, 2 Hz, 3H); 0.90 (d, 6.8 Hz, 3H); 0.96 (s, 3H); 2.44 (s, 3H); 5.3 (m, 1H); 7.33 (d, 8.0 Hz, 2H); 7.79 (d, 8.3 Hz, 2H). $^{13}$C NMR: (100 MHz, CDCl$_3$) δ: 144.52 (C32), 139.00 (C4), 134.85 (C35), 129.87 (C34, C36), 127.77 (C33, C37), 123.65 (C7), 82.54 (C2), 56.79 (C11), 56.25 (C17), 50.05 (C10), 42.43 (C12), 39.80 (C22), 39.65 (C13), 39.01 (C3), 37.03 (C5), 36.49 (C20), 36.31 (C18), 35.89 (C6), 31.99 (C9), 31.89 (C8), 28.77 (C1), 28.33 (16), 28.15 (C15), 24.38 (C23), 23.95 (C21), 22.95 (C25), 22.70 (C24), 21.77 (C38), 21.13 (C14), 19.28 (C26), 18.84 (C19), 11.98 (C27).

Preparation of Cholesterol-Tetraethylene Glycol (B)

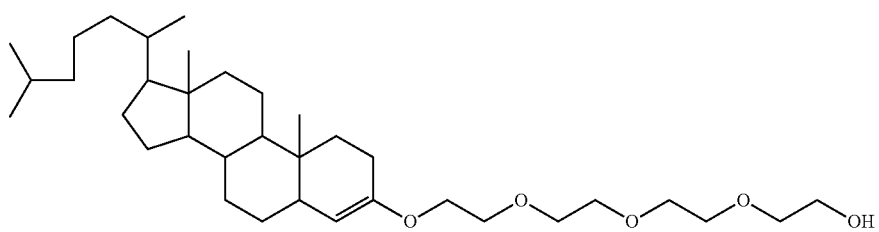

(B)

Into a flask, 0.503 g of cholesterol tosyl (A) was added and dissolved in 5 mL of anhydrous 1,4-dioxane. 3.591 g of tetraethylene glycol (20 eq.) were added on this solution and the mixture was reacted for 4 h at reflux under argon atmosphere. The resulting solution was concentrated to dryness and then dissolved in 20 mL of DCM and washed with 2×20 mL sat. NaHCO$_3$, 3×20 mL H$_2$O, 1×20 mL sat. NaCl. The resulting aqueous phases were extracted again with 20 mL DCM. Finally, after combining the organic phases were dried over MgSO$_4$, filtered and the solvent was evaporated to dryness. The purification of crude was carried out by chromatography with basic alumina (DCM/MeOH 0-5%). 0.260 g of product as a yellowish oil were obtained (50%).

HPLC-PDA: (C$_{18}$, 5-100% B, A: ACN B: MeOH, 4.5 min, 2 mL/min, λ=210 nm) r$_T$: 2.6 min (73% 210 nm). $^1$H NMR: (400 MHz, CDCl$_3$) δ: 0.67 (s, 3H); 0.85 (d, 1.6 Hz, 3H); 0.87 (d, 1.6 Hz, 3H); 0.91 (d, 6.4 Hz, 3H); 0.99 (s, 3H); 3.18 (m, 1H); 3.67 (m, 16H). $^{13}$C NMR: (100 MHz, CDCl$_3$) δ: 141.07 (C4), 121.71 (C7), 79.69 (C2), 72.82-70.40 (C30, C32, C33, C35, C36, C38), 67.36 (C29), 61.87 (C39), 56.93 (C11), 56.30 (C17), 50.33 (C10), 42.47 (C12), 39.93 (C22), 39.66 (C13), 39.11 (C3), 37.37 (C5), 37.01 (C6), 36.33 (C20), 35.92 (C18), 32.09 (C8), 32.04 (C9), 28.43 (C1), 28.37 (C16), 28.15 (C15), 24.43 (C23), 23.97 (C21), 22.96 (C24), 22.70 (C25), 21.21 (C14), 19.51 (C26), 18.86 (C19), 12.00 (C27).

Preparation of Cholesterol-Tetraethylene Glycol-DSC (C)

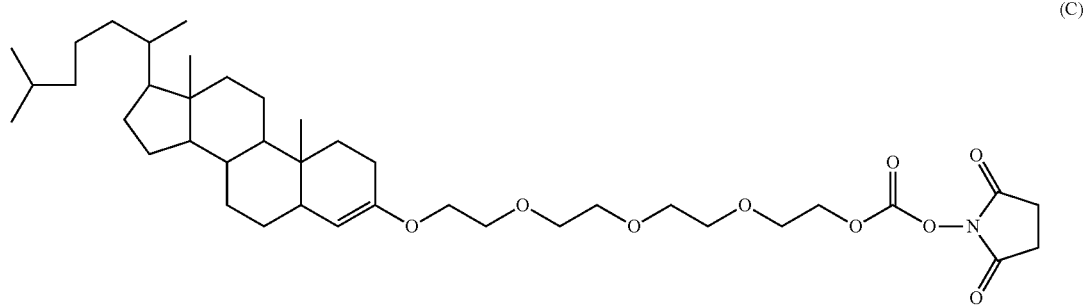 [SMILES: CC(C)CCCC(C)C1CCC2C3CCC4C=C(OCCOCCOCCOCCOC(=O)ON5C(=O)CCC5=O)CCC4(C)C3CCC12C]

(C)

The compound B (1 eq., 0.2746 g) was dissolved in 9 mL of a mixture of DCM:ACN:DIPEA (1:1:1) and added DSC (3 eq., 0.2746 g). The mixture was stirred under argon atmosphere and after 16 h it was noted the disappearance of the starting product B. The solvent was evaporated to dryness and the crude was dissolved in 5 mL DCM. This organic phase was washed with 5 mL of water. The organic phase was dried over $MgSO_4$, filtered, and finally, the solvent was evaporated to dryness. The crude was used in the following reaction without any further purification.

Preparation of cRGDfK (D)

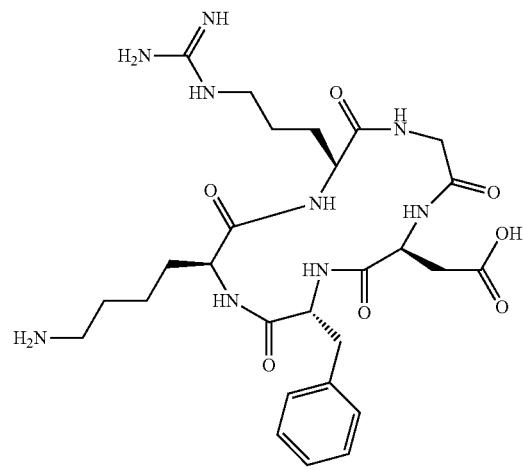

(D)

The synthesis of D-peptide was carried out as described in Dai X., et. al. "An improved synthesis of a selective αvβ3-integrin antagonist cyclo (-RGDfK)" *Tetrahedron Letters* 2000, vol. 41, pp. 6295-6298, with minor modifications. Briefly, the final cyclic peptide was deprotected with a mixture of $TFA/TIS/H_2O$ (95:2.5:2.5) and purified by RP-HPLC, obtaining the D-peptide (180.9 mg, 15%) as a white solid.

HPLC-MS: ($C_{18}$, 5-100% B, A: ACN B: $NH_4HCO_3$ 20 mM, 3.5 min, 1.6 mL/min, λ=210 nm) $r_T$: 2.47 min, m/z=604.3 [M+H]$^+$, Calculated mass: 603.67 (99% 210 nm). MALDI-TOF (ACH): 604.24 [M+H]$^+$. ANALYSIS OF AMINO ACIDS: Asp: 0.673, Gly: 0.734, Arg: 0.780, Lys: 0.677, Phe: 0.632

Preparation of Cholesterol-cRGDfK (E)

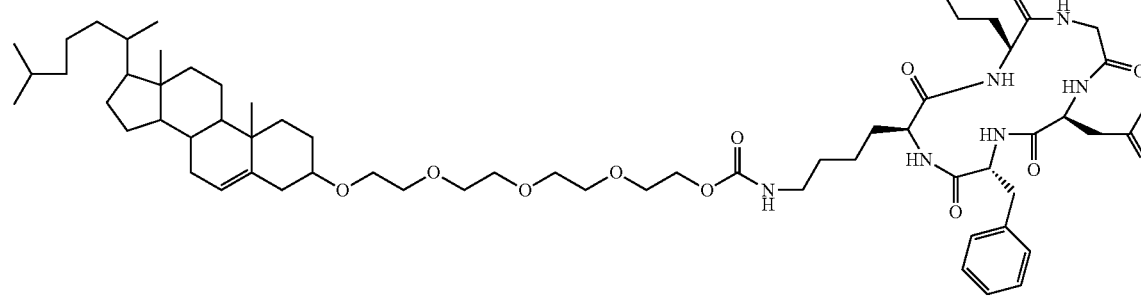

(E)

Compound C (1.5 eq., 69.00 mg) was dissolved in 5 mL of anhydrous DMF and DIPEA (2 eq., 32 µL) and D-peptide (1 eq., 65.95 mg) were added. The reaction was left under stirring for 16 h until the disappearance of the D-peptide (control by HPLC-MS). The solvent was removed and the crude was precipitated from TMBE (3×). The compound E was obtained as a white solid (55.5 mg, 74%). HPLC-MS: (Symmetry300 $C_4$, 5-100% B, A: ACN B: $H_2O$, 30 min, 1 mL/min, $\lambda$=210 nm) $r_T$: 17.31 min, m/z=1192.8 $[M+H]^+$, Calculated mass: 1192.53. HPLC-PDA: ($C_4$, 5-100% B, A: ACN B: $H_2O$, 30 min, 1 mL/min, $\lambda$=210 nm) $r_T$: 20.1 min (98% 210 nm). ANALYSIS OF AMINO ACIDS: Asp: 0.99, Gly: 1.18, Arg: 1.15, Lys: 0.92, Phe: 1.04

Example 1b (Comparative with Example 1a): Preparation of Conjugates with Carbamate Bond Preparation of Cholesterol-DCl (F)

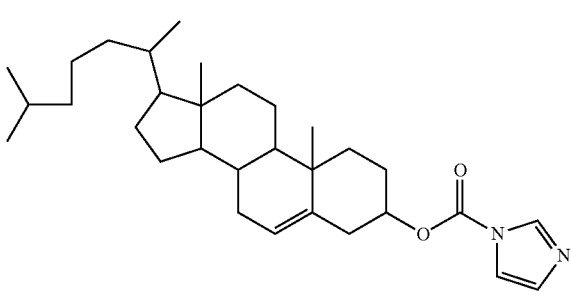

(F)

The cholesterol (1 eq., 200.2 mg) was dissolved in 9 mL of a mixture of DCM/DIPEA/ACN (1:1:1) and to this the CDI (10 eq., 852.1 mg) was added. It was allowed to react overnight, and the appearance of the desired product was observed. The solvent was evaporated to dryness and the crude was dissolved in 5 mL DCM. This organic phase was washed with 5 mL of water. The organic phase was dried over $MgSO_4$, filtered and finally the solvent was evaporated to dryness. The crude was used in the following reaction without any further purification.

Preparation of Cholesterol-Tetraethylene Glycol Carbamate (G)

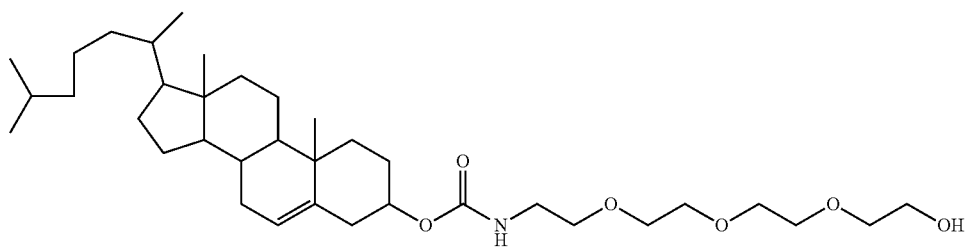

(G)

The compound F (1 eq., 109.6 mg) was taken and dissolved in DCM, to this solution was added 1-amino-3,6,9-trioxaundecanyl-11-ol (4.5 eq., 152.8 mg) and the solution was then set to pH 8 using DIPEA. The mixture was allowed to react, monitoring its progress by HPLC-MS, until it was observed the disappearance of the starting product F. The crude was washed making extractions from the organic phase with water. The organic phase was dried over $MgSO_4$, filtered and finally the solvent was evaporated to dryness. The final crude was purified by silica column (Isocratic AcOEt) to obtain 80.2 mg of compound G as a yellowish oil (60%). HPLC-MS: (XSelect $C_{18}$, 5-100% B, A: ACN B: MeOH, 4.5 min, 2 mL/min, $\lambda$=210 nm) $r_T$: 1.87 min m/z=606.47 $[M+H]^+$, Calculated mass: 605.89. HPLC-PDA: ($C_4$, 5-100% B, A: ACN B: $H_2O$, 30 min, 1 mL/min, $\lambda$=210 nm) $r_T$: 21.8 min (95% 210 nm) $^1$H NMR: (400 MHz, $CDCl_3$) $\delta$: 0.680 (s, 3H); 0.86 (d, 1.8 Hz, 3H); 0.87 (d, 1.8 Hz, 3H); 0.91 (d, 6.5 Hz, 3H); 1.01 (s, 3H); 3.36 (m, 1H); 3.65 (m, 16H). 13C NMR: (100 MHz, $CDCl_3$) $\delta$: 156.58 (C29), 140.07 (C4), 122.53 (C3), 70.74 (C8), 70.56-70-25 (C33, C35, C36, C38, C39, C41), 61.79 (C42), 56.83 (C14), 56.27 (C15), 50.15 (C6), 42.45 (C13), 40.85 (C32), 39.88 (C22), 39.66 (C12), 38.75 (C7), 37.15 (C5), 36.71 (C10), 36.32 (C20), 35.93 (C18), 32.05 (C1), 32.02 (C2), 28.37 (9), 28.35 (C17), 28.15 (C16), 24.43 (C23), 23.97 (C21), 22.96 (C24), 22.70 (C25), 21.18 (C11), 19.48 (C19), 18.85 (C27), 12.00 (C26).

Preparation of Cholesterol-Tetraethylene Glycol-DSC Carbamate (H)

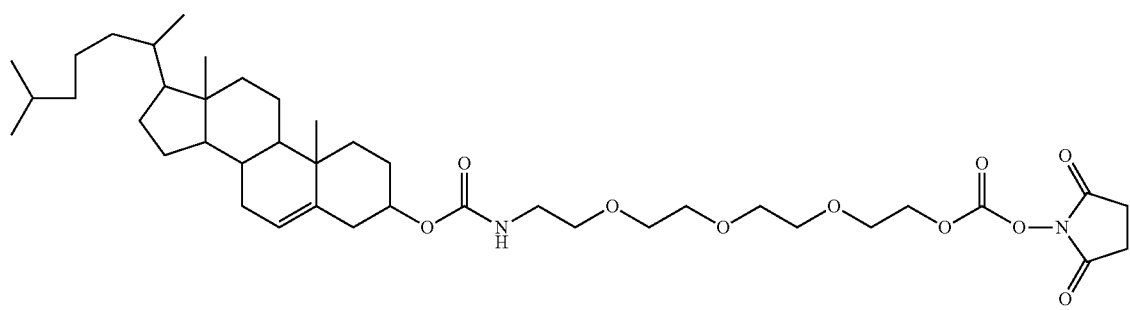

(H)

The compound G (1 eq., 80.2 mg) was taken and reacted with DSC (10 eq., 316.8 mg) in 9 mL of a DCM/DIPEA/ACN mixture (1:1:1) for 16 h. When the disappearance of the compound G was detected, the solvent was evaporated to dryness and the crude was dissolved in 5 mL of DCM and washed with water. The organic phase was dried over $MgSO_4$, filtered and the solvent was evaporated, obtaining a crude ready to use without any further purification.

Preparation of Cholesterol-cRGDfK Carbamate (I)

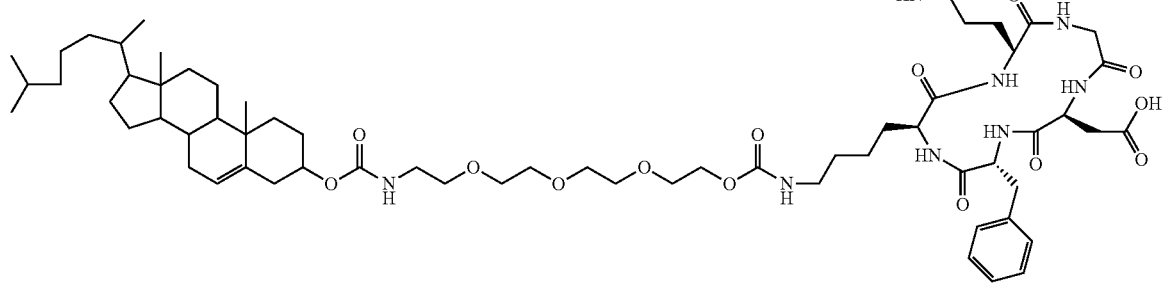

(I)

The entire compound H was dissolved in 5 mL of anhydrous DMF and DIPEA (2 eq., 60 µl) and D-peptide (1 eq., 51.2 mg) were added. The reaction was allowed under stirring for 16 h until the disappearance of the D-peptide (control by HPLC-MS). The solvent was removed and the crude was precipitated from TMBE (3×), finally washed with water. In this way 17 mg of the product I were obtained as a white solid.

HPLC-MS: (XSelect $C_{18}$, 5-100% B, A: ACN B: MeOH, 4.5 min, 2 mL/min, λ=210 nm) $r_T$: 1.03 min, m/z=1235.94 [M+H]$^+$, Calculated mass: 1235.55. HPLC-PDA: ($C_4$, 5-100% B, A: ACN B: $H_2O$, 30 min, 1 mL/min, λ=210 nm) $r_T$: 19.91 min (86% 210 nm). ANALYSIS OF AMINO ACIDS: Asp: ND, Gly: 1.23, Arg: 1.11, Lys: ND, Phe: 1.11.

Example 2. General Method for the Preparation of Vesicles

The vesicles carrying the conjugates of the invention (ether bond) or the conjugates of the state of the art (carbamate bond) were prepared as is described below, based on a procedure described elsewhere (Cano-Sarabia, M. et. al. "Preparation of Uniform Rich Cholesterol Unilamellar Nanovesicles Using CO2-Expanded Solvents" Langmuir 2008, vol. 24, pp. 2433-2437).

The method for the preparation of vesicles was carried out in an assembly such as that represented in FIG. 1. The assembly consisted of a high pressure reactor (R) to which was added a solution with the components of the vesicle membrane in ethanol at a certain concentration (C1, C2 . . . Cn depending on the number of components), at atmospheric pressure and at the working temperature ($T_w$=T). In a second step, compressed $CO_2$ was added up to the working pressure ($P_w$=P), yielding the volumetric expansion of the solution to a molar ratio $X_{CO2}$. The addition was carried out using the pump P1 through the valve V-1, keeping closed the rest of the valves. The system was maintained at a pressure P and temperature T for a certain amount of time to ensure the total homogenization and the thermal equilibrium. After this time, V-4 was opened with the purpose of connecting the reactor R with the filter FL, previously pressurized with $N_2$ up to $P_w$, keeping closed the rest of the valves. The opening of V-6 allowed the depressurization of the volumetrically expanded solution on an aqueous solution pumped through P2. In this final step, a stream of $N_2$ added through V-2 to $P_w$ was used as a plunger to push the expanded solution, and to maintain the working pressure constant in the reactor during the step of depressurization. The presence of the filter FL allowed to collect any precipitates formed during the process. The vesicles formed were collected in the vessel C, and then stored in glass bottles at 4° C. Once the depressurization was completed, V-6 and V-2 were closed and depres surization of the equipment by opening again V-6 was carried out.

Example 3. Preparation of Vesicles of DPPC:Cholesterol:Cholesterol-PEG-RGD by the Compressed Fluid Technology First a solution of 8 mg of Cholesterol, 24 mg of DPPC and 4 mg of conjugate (cholesterol-PEG-RGD) in 1.2 mL of ethanol was introduced in a high pressure reactor with a volume of 7.5 mL, at atmospheric pressure and working temperature ($T_w$=35 C). Compressed $CO_2$ was added, yielding the volumetric expansion of the solution to a molar ratio $X_{CO2}$=0.8 and a working pressure $P_W$=10 MPa. To achieve the total homogenization and thermal equilibrium, the system was left for approximately 60 minutes at 10 MPa and 35° C. Finally, the expanded organic solution was depressurized from the working pressure to the atmospheric pressure, over 24 mL of an aqueous solution. In this last step, a stream of $N_2$ at 10 MPa was used as a plunger to push the cholesterol solution in ethanol in order to maintain the working pressure constant in the reactor during the depressurization. The vesicles were then transferred to a vessel which, when sealed, was stored at 5±3° C. until use.

As a result, vesicles of DPPC:Cholesterol:cholesterol-PEG-RGD (10:6:1) were obtained with a microscopic appearance, average size and Z-potential shown in the Table 1.

The average size, particle-size distribution and Z-potential were determined by DLS (Dinamic Light Scattering) at a temperature of 25 degrees Celsius.

Table 1 shows the results of physical appearance, average particle size and Z-potential of different batches of vesicles DPPC:cholesterol:cholesterol-PEG-RGD.

TABLE 1

| Composition | Average size[3] (nm) (±SD)[4] | PDI[3] (±SD)[4] | Z-Potential[3] (mV) (±SD)[4] |
|---|---|---|---|
| DPPC:Chol:Chol-PEG-RGDether[1] | 152.7 (±0.8) | 0.182 (±0.010) | +32.4 (±2.4) |
| (1.3 mM:0.8 mM:0.1 mM) | 128.8 (±0.2) | 0.235 (±0.017) | +30.4 (±1.4) |
| DPPC:Chol:Chol-PEG-RGDcarb[2] | 141.5 (±1.8) | 0.357 (±0.005) | −9.5 (±0.2) |
| (1.3 mM:0.8 mM:0.1 mM) | 117.9 (±0.6) | 0.357 (±0.008) | −0.9 (±0.3) |

[1]Vesicles of DPPC:Cholesterol:Cholesterol-PEG-RGD with ether bond,
[2]Vesicles of DPPC:Cholesterol:Cholesterol-PEG-RGD with carbamate bond,
[3]Measurements of DLS carried out by an instrument Nano-ZS (Malvern Instruments, United Kingdom).
PDI: Polydispersity index
[4]SD: Standard deviation of three consecutive measurements on the same batch.

Figure 2:
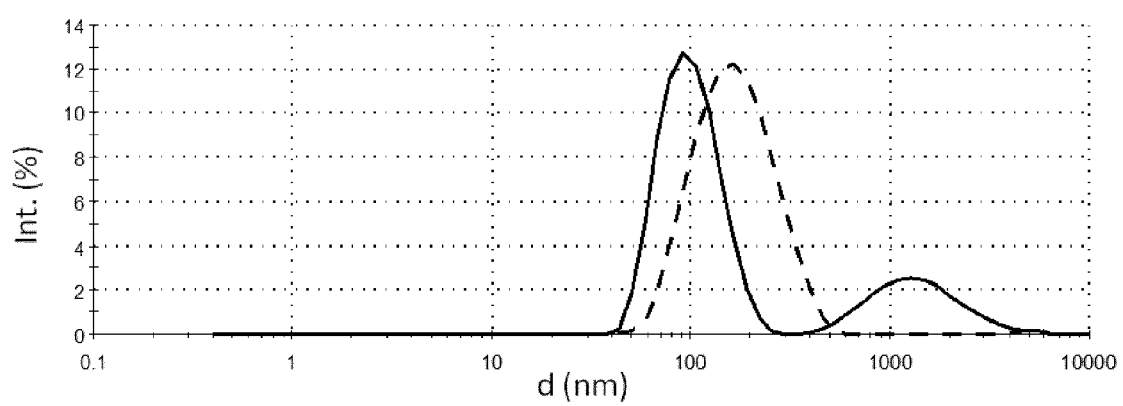
FIG. 2. Particle-size distribution of vesicles containing conjugates of the invention (with ether bond, in dashed line) and vesicles containing conjugates with carbamate bond (in solid line). In the figure it is shown that the former have a monomodal distribution, while the latter show a bimodal, less homogeneous distribution.

In regard to the macroscopic appearance of different formulations, it was observed that both the vesicles prepared using Cholesterol-PEG-RGD with ether bond and the vesicules prepared using Cholesterol-PEG-RGD with carbamate bond had the appearance of an opalescent, dispersed solution. On the other hand, it was noted that in the case of vesicles of DPPC:Cholesterol:Cholesterol-PEG-RGD with ether bond the different preparations of vesicles had no stability problems in the short term, with small average size and polydispersity index, which make them attractive from the pharmaceutical point of view. Such polydispersity index is higher in the case of vesicles Cholesterol-PEG-RGD with carbamate bond, the distribution of which is bimodal, in contrast to the monomodality found for vesicles containing Cholesterol-PEG-RGD with ether bond (FIG. 2). For this latter system higher Z-potentials were found (around +30 mV), falling within the value range considered to allow the colloidal stability of dispersed systems over time. It was therefore concluded that in terms of both particle size and suspension stability, vesicles having conjugates with the ether bond have better properties than the vesicles having conjugates with the carbamate bond.

Example 4. Internalization Experiments

In order to assess whether the liposomes carrying the conjugates of the invention have superior properties in terms of intracellular delivery of their contents in comparison with liposomes carrying conjugates of the prior art, an experiment of internalization of the contents of the liposomes in a cell line was carried out. The substance delivered was a dye that can be easily monitored by fluorescence.

Liposome Labelling

For liposome labelling, 500 µL of plain liposomes (DPPC:Col liposomes) were directly mixed with 25 µL of a Did ethanolic solution (1 µM) for a final concentration of 50 nm of the dye in the membrane. After 30 min of mixing, free DiD was separated from the total sample by gel filtration. For this purpose pre-packed columns (PD SpinTrap G-25) were three times equilibrated with PBS buffer and then 130 µL of sample was added. The separation took place by spin centrifugation at 800×g.

The procedure described above was repeated analogously for the other liposome types.

Cell Culture.

CDC/EU.HMEC-1 (HMEC-1) cells were provided by Centers for Disease Control and Prevention (CDC-NIDR). HMEC-1 is an immortalized human microvascular endothelial cell line that retains the morphologic, phenotypic, and functional characteristics of normal human microvascular endothelial cells. HMEC-1 cells were maintained in MCDB 131 (Invitrogen) supplemented with 50 units ml-1 penicillin, 50 µg ml-1 streptomycin, 10 mM L-glutamine and 10% fetal bovine serum (FBS) in a 37° C. humidified atmosphere with 5% CO2. All the media, serum and antibiotics were purchased from Invitrogen.

Cellular Uptake of Liposomes Assessed by Laser Scanning Confocal Microscopy (LSCM).

HMEC-1 cells were seeded onto Fluorodish culture plates (World Precision Instruments, Sarasota, Fla.) at a density of 2×105 cells per plate and allowed to grow for 36-48 hours. 50 µl of DiD-labelled Liposomes (DPPC:Col) or DiD-labelled Liposome-RGD conjugates (DPPC:Col:Col-PEG-RGDether liposomes and DPPC:Col:Col-PEG-RGDcarbamate liposomes) (1.5 mg/ml) were mixed with 200 µl MCDB 131 medium, added into the cells and incubated for 3 h at 37° C. in a humidified atmosphere with 5% CO2. Subsequently, cells were washed with serum-free MCDB 131 and incubated at 37° C. for 5 min with Lysotracker Green DND-26 (50 nM, Molecular probes, Eugene, Oreg.) to label the endosomal/lysosomal compartments. Cells were examined under an inverted Leica SP5 laser scanning confocal spectral microscope (Leica Microsystems Heidelberg GmbH, Mannheim, Germany) using a 60×1.42 NA oil immersion objective. To visualize two colours of fluorescence simultaneously, we used the 514 nm line from Argon laser for Lysotracker green and the 630 nm line from a He—Ne laser for Did.

Figure 3:
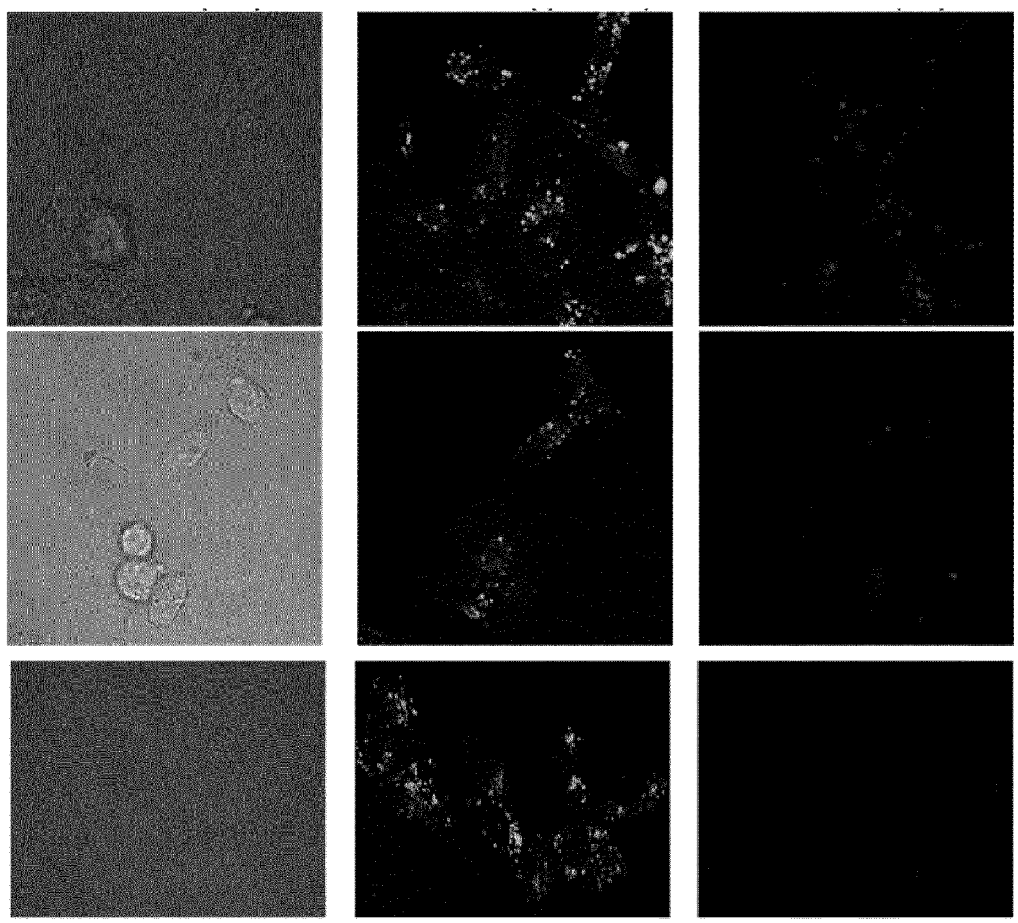
FIG. 3. Confocal images showing the results of the internalization experiments for liposomes bearing no conjugate, bearing DPPC:Col:Col-PEG-RGD(ether) and bearing DPPC:Col:Col-PEG-RGD(carbamate).
Left-hand side, middle and right-hand side columns correspond to Transmission (Cells), Green Channel (Lysosomes) and Red Channel (DiD) respectively. Upper, middle and lower rows correspond to DPPC:Col:Col-PEG-RGD(ether), DPPC:Col:Col-PEG-RGD(carbamate) and DPPC:Col respectively.

Confocal Images for DPPC:Col:Col-PEG-RGDether liposomes (top), DPPC:Col:Col-PEG-RGDcarbamate liposomes (middle) and DPPC:Col (bottom) liposomes are shown in FIG. 3. The spots observed in the red channel (right-hand side column) show the presence of labelled liposomes internalized by the cells. It is clearly observed that for DPPC:Col:Col-PEG-RGDether liposomes this internalization is higher in comparison with the other two.

Flow Cytometry.

HMEC-1 cells were seeded at densities of 2×105 cells ml-1 on Fluorodish culture plates (World Precision Instruments, Sarasota, Fla.) 36-48 h prior to experiment. Cells were incubated with DiD-labelled Liposomes (DPPC:Col) or DiD-labelled Liposome-RGD conjugates (DPPC:Col:Col-PEG-RGDether liposomes and DPPC:Col:Col-PEG-RGDcarbamate liposomes) (0.3 mg/ml) resuspended into MCDB 131 supplemented with 10 mM L-Glutamine without FBS for 3 hours at 37° C. Cells were subsequently washed twice with Dulbecco's phosphate buffered saline (DPBS) solution, detached using trypsin and resuspended in cell culturing medium before subjecting to fluorescence-activated cell sorting analysis. Data acquisition and analysis was performed using FACS scan (Beckton-Dickinson) and BD FACSDiva software. 10.000 viable cells were evaluated in each experiment.

Figure 4:
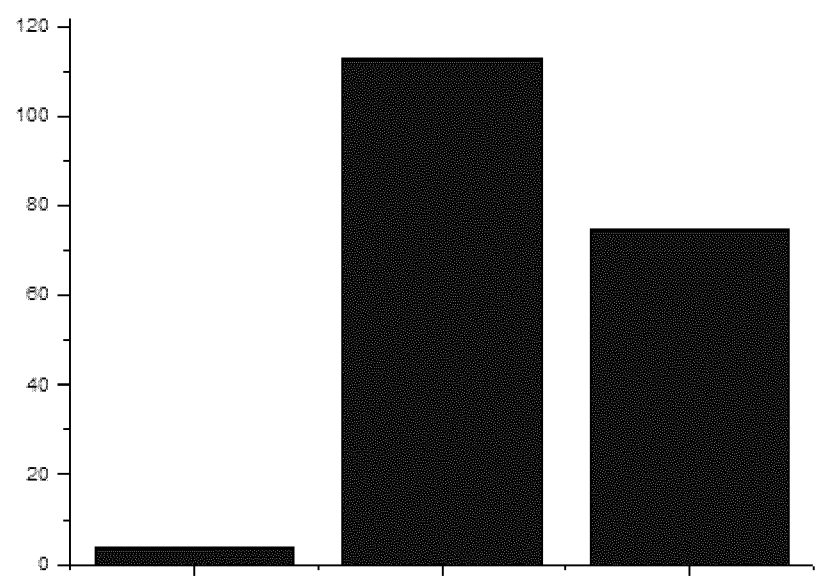
FIG. 4. Shows the fluorescence intensity associated to the cells that have internalized the DID-labelled liposomes. It is shown that this internalisation is significantly higher when using DPPC:Col:Col-PEG-RGD(ether) liposomes than when using DPPC:Col:Col-PEG-RGD(carbamate) and DPPC:Col liposomes.
The y axis shows Fluorescence Intensity (a.u.). In the x axis: the left-hand side value, middle value and right-hand side value correspond to plain liposomes, liposomes with the DPPC:Col:Col-PEG-RGD(ether) conjugate and liposomes with the DPPC:Col:Col-PEG-RGD(carbamate) conjugate respectively.

In FIG. 4 it can be seen the fluorescence intensity associated to the cells that have internalized the DID-labelled liposomes. It is shown that this internalisation is significantly higher when using DPPC:Col:Col-PEG-RGDether bearing liposomes than when using DPPC:Col:Col-PEG-RGDcarbamate bearing liposomes or simple DPPC:Col liposomes bearing no conjugate.

Example 5. In Vitro Activity Experiments

Activity Assays:

Primary cultures of mouse aortic endothelial cells (MAEC) of GLA (alpha galactosidase) deficient mice (Glat-mKul1) were isolated following procedures previously described (Shu L., et al. "An in vitro model of Fabry disease" *J. Am. Soc. Nephrol.* 2005, vol. 16, pp. 2636-45). Endothelial origin of isolated cells was confirmed by CD105 staining.

For activity assays, cells in passages 2 to 5 were seeded in 24 well plates and maintained at 37° C. and 5% of CO2. Twenty-four hours after seeding 8 µM of NBD-Gb3 (Matreya) was added to the cultures along with the specified concentrations of tested compounds (free enzyme—alpha-galactosidase, enzyme containing liposomes or empty liposomes). After 48 h incubation, cells were trypsinized and Gb3-NBD fluorescent signal was analyzed by flow cytometry (FacsCalibur, Beckton Dickinson). To calculate the percentage of Gb3-NBD signal, fluorescent signal in control cells (without treatment) was established as 100% and the rest of the values were normalized accordingly. Since alpha-galactosidase activity reduces those Gb3 deposits, the percentage of Gb3 loss (% Gb3 loss=100–% Gb3-NBD signal) was used to plot the results.

Figure 5:
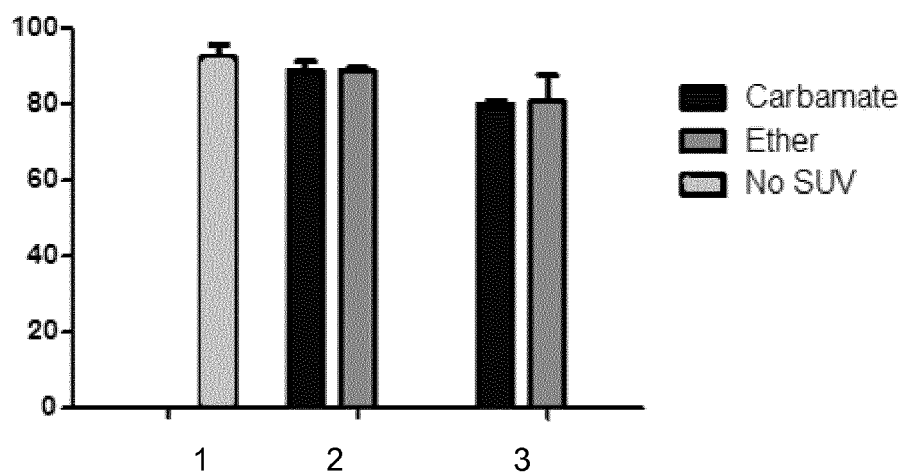
FIG. 5. Alpha galactosidase activity of liposomes in MAEC cultures of alpha galactosidase-deficient mice, at a concentration of 1.5 µg/ml of enzyme. The y axis depicts % Gb3 loss (mean+/−standard deviation). In the x axis: point 1 corresponds to alpha-galactosidase (no liposome encapsulation), point 2 corresponds to functionalized liposomes (either with carbamate or ether linked conjugates) and point 3 corresponds to the functionalized liposomes which have been diafiltered.

It can be seen in FIG. 5 the alpha galactosidase activity of liposomes in MAEC cultures of alpha galactosidase-deficient mice. 1.5 µg/mL of free enzyme (alpha-galactosidase-histogram bar number 1 in FIG. 5) reduced the Gb3 deposits in 92.32%. Liposomes incorporating the same enzyme reduced the Gb3 deposits similarly (88.9%) independently of having carbamate or ether linkage (histogram bars number 2 in FIG. 5). Purification of liposomes by diafiltration reduced slightly this activity (histogram bars number 3 in FIG. 5), however, it is worth noting that the concentration of the enzyme in these purified liposomes will be lower than 1.5 µg/mL, since just a fraction (usually around 80%) of the total enzyme used in the liposome preparation is finally encapsulated.

Figure 6:
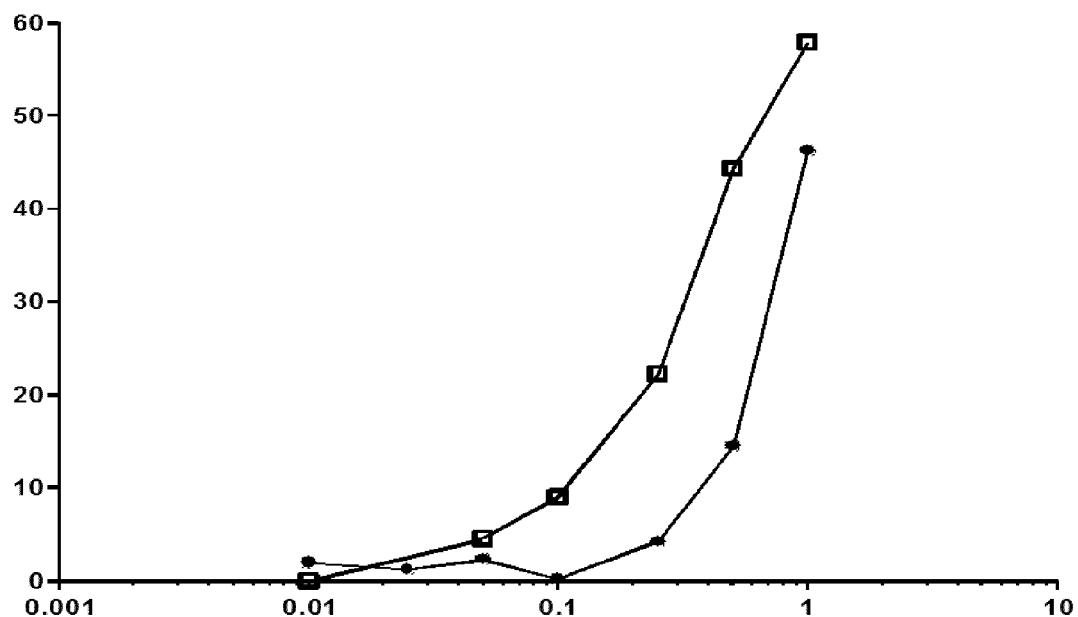
FIG. 6. Effect of the diafiltered conjugate-bearing liposomes carrying alpha-galactosidase at different concentrations on the loss of Gb3 in alpha-galactosidase deficient endothelial cells. The x axis shows % Gb3 loss whereas the y axis shows the alpha-galactosidase concentration (µg/mL). The line with the solid black dots corresponds to liposomes bearing conjugates with the carbamate bond, whereas the line with the empty squares corresponds to liposomes bearing conjugates with the ether bond.

It is also shown in FIG. 6 that the diafiltered liposomes carrying the conjugates with the ether bond have a higher activity than those carrying the conjugates with the carbamate bond at varying concentrations.

Example 6. Improvement of Specific Enzymatic Activity Due to the Encapsulation of Alpha-Galactosidase in the Liposomes Bearing the Conjugates of the Invention (with an Ether Bond)

Production of Recombinant GLA (Alpha-Galactosidase)

The expression vector pOpinE-GLA encodes a full-length version of the human α-galactosidase (GLA) gene, cloned into pOPINE plasmid (Berrow N S, et al. "A versatile ligation-independent cloning method suitable for high-throughput expression screening applications" *Nucleic Acids Res* 2007, vol. 35, e45). The suspension-adapted HEK (human embryonic kidney) cell line FreeStyle™ 293 F (Gibco, Invitrogen corporation) was used to produce recombinant GLA by means of PEI-mediated transient gene expression. Details of GLA production and purification have been previously described (Corchero J L, et al., "Integrated approach to produce a recombinant, his-tagged human alpha-galactosidase a in mammalian cells", *Biotechnol Prog.* 2011, vol. 27, pp. 1206-1217).

Detection and Quantification of Recombinant GLA Encapsulated into Liposomes

To estimate the incorporation of recombinant GLA into liposomes, samples from 1) initial GLA in water, 2) GLA mixed with lipids, 3) purified liposomes and 4) water containing free, non-encapsulated GLA, were mixed with denaturing, loading buffer and analyzed by SDS-PAGE and further western-blot developed with a rabbit polyclonal anti-GLA serum from Santa Cruz Biotechnology (a-gal A H-104: sc-25823) and a goat anti-rabbit IgG HRP-conjugate (Bio-Rad Laboratories, Inc., cat. #170-6515) as secondary antibody. Amounts of recombinant GLA within each of the above mentioned samples were estimated by comparison with known amounts (usually ranging from 25 to 125 ng) of a recombinant GLA previously produced, purified, and quantified in our laboratory. Samples to be quantitatively compared were run in the same gel and processed as a set. Densitometric analyses of the bands were performed with the Quantity One software (Bio-Rad Laboratories, Inc). Percentage of encapsulated GLA was obtained by comparison of amounts of GLA found in purified liposome fractions with total, initial amount of GLA added.

Characterization of Recombinant GLA Encapsulated into Liposomes

The enzymatic α-galactosidase activity of GLA found into the different samples was assayed, in vitro, fluorometrically as described by Desnick et al. (Desnick R J, et al. "Fabry's disease: enzymatic diagnosis of hemizygotes and heterozygotes. Alpha-galactosidase activities in plasma, serum, urine, and leukocytes", *J. Lab. Clin. Med.* 1973, vol. 81, pp. 157-171) with the modifications of Mayes et al. (Mayes J S., et al. "Differential assay for lysosomal alpha-galactosidases in human tissues and its application to Fabry's disease" *Clin. Chim. Acta* 1981, vol. 112, pp. 247-251). Briefly, enzymatic activity was assayed using as substrate 4 methylumbelliferyl α D-galactoside (4MUG, Sigma Chemical), at a concentration of 2.46 mM in assay buffer (0.01 M acetic acid, pH 4.5). A typical assay reaction mixture contains 100 µl of substrate and 25 µl of enzyme sample. Enzymatic reactions took place in agitation, at 37° C. for 1 hour, and were stopped with 1.25 mL of 0.2 M glycine-NaOH buffer (pH 10.4). The released product (4-methylumbelliferone or 4-MU) was determined by fluorescence measurement at 365 and 450 nm as excitation and emission wavelengths, respectively. Samples containing from 0 to 500 ng 4-MU/ml of commercial 4-MU (Sigma Chemical) in 0.2 M glycine-NaOH buffer (pH 10.4) were used to create a standard curve to calibrate the readings. Specific enzymatic activities are expressed as µmol 4-MU/h/mg protein.

Stability of Recombinant GLA into Liposomes.

The stability of GLA into the different samples was assayed by following their specific enzymatic activity. After their preparation ("Day zero"), GLA protein amount and enzymatic activity were determined (as described before) for each sample. With those values, initial specific enzymatic activity was determined. Samples were kept in water at 4° C., and at different time points, enzymatic activity was assayed. Using initial amounts of GLA, specific enzymatic activities were recalculated and compared to that determined at "Day zero", used as a reference.

Efficiency of Encapsulation of GLA into the Liposomes.

For each encapsulation experiment, the following samples were obtained and analyzed:
1. Initial GLA (before encapsulation).
2. Total GLA, that is, the result of adding the lipids to point 1 and encapsulating a fraction of the initial GLA. Total means both encapsulated and non-encapsulated GLA. The separation of GLA encapsulating liposomes from free GLA remaining in solution gives points 3 and 4.
3. Liposome-encapsulated-GLA, that is, only GLA which has been encapsulated.
4. Free GLA, that is, GLA which has not been encapsulated.

The encapsulation efficiency of GLA into the vesicles, as determined by SDS-PAGE and further western-blot in different experiments, is shown in the next table:

| Experiment # | Sample | µg GLA/ml | Efficiency of GLA encapsulation |
|---|---|---|---|
| A | "Total" (2) | 3.87 | |
|   | SUVs-GLA (3) | 0.63 | 16% |
|   | Free GLA (4) | 3.67 | 95% |
| B | "Total" (2) | 4.17 | |
|   | SUVs-GLA (3) | 1.23 | 29% |
|   | Free GLA (4) | 2.53 | 61% |
| C | "Total" (2) | 4.31 | |
|   | SUVs-GLA (3) | 0.97 | 23% |
|   | Free GLA (4) | 3.88 | 90% |
| D | "Total" (2) | 7.90 | |
|   | SUVs-GLA (3) | 2.32 | 29% |
|   | Free GLA (4) | 5.30 | 67% |
| E | "Total" (2) | 7.70 | |
|   | SUVs-GLA (3) | 2.27 | 29% |
|   | Free GLA (4) | 3.90 | 51% |
| F | "Total" (2) | 6.40 | |
|   | SUVs-GLA (3) | 2.28 | 36% |
|   | Free GLA (4) | 3.40 | 53% |

According to these results, the efficiency of GLA encapsulation into vesicles is of 27+/−6.8% (mean+/−standard deviation).

| Experiment # | Sample | Specific enzymatic avtivity µmol 4MU/h/mg GLA |
|---|---|---|
| A | Initial GLA (1) | 312 |
|   | Total (2) | 1349 |
|   | SUVs-GLA (3) | 1570 |
| B | Initial GLA (1) | 362 |
|   | Total (2) | 1112 |
|   | SUVs-GLA (3) | 957 |
| C | Initial GLA (1) | 221 |
|   | Total (2) | 1239 |
|   | SUVs-GLA (3) | 1716 |
| D | Initial GLA (1) | 109 |
|   | Total (2) | 1542 |
|   | SUVs-GLA (3) | 1750 |
| E | Initial GLA (1) | 81 |
|   | Total (2) | 1454 |
|   | SUVs-GLA (3) | 1780 |
| F | Initial GLA (1) | 109 |
|   | Total (2) | 2001 |
|   | SUVs-GLA (3) | 1934 |

The addition to the GLA solution of lipids that will form the vesicles results in a significant increase in the specific enzymatic activity of the encapsulated enzyme.

As can be seen, the specific enzymatic activity of "Total" samples (GLA mixed with the lipids that form the vesicles) clearly increases (from 4- to 18-fold) when compared to initial GLA, still not associated with vesicles or their components.

REFERENCES CITED IN THE APPLICATION

Torchilin V. "Recent advances with liposomes as pharmaceutical carriers". Nature Rev. Drug Disc. 2005, vol. 4, pp. 145-160.

Dubey P., et. al. "Liposomes modified with cyclic RGD peptide for tumor targeting". J. Drug Targ. 2004, vol. 12, pp. 257-264.

Negishi Y., et. al. "Preparation and characterization of laminin-derived peptide AG73-coated liposomes as a selective gene delivery tool". Biol. Pharm. Bull. 2010, vol. 33, pp. 1766-1769.

Pan X., et. al. "Synthesis of cetuximab-immunoliposomes via a cholesterol-based membrane anchor for targeting of EGFR". Bioconjugate Chem. 2007, vol. 18, pp. 101-108.

Thomson B., et. al. "Neutral postgrafted colloidal particles for gene delivery". Bioconj. Chem. 2005, vol. 16, pp. 608-614.

Boomer J., et. al. "Cytoplasmic delivery of liposomal contents mediated by an acid-labile cholesterol-vinyl ether-PEG conjugate" Bioconj. Chem. 2009, vol. 20, 47-69.

Dai X, et. al. "An improved synthesis of a selective $\alpha v \beta 3$-integrin antagonist cyclo (-RGDfK)" Tetrahedron Letters 2000, vol. 41, pp. 6295-6298.

Berrow N S, et al. "A versatile ligation-independent cloning method suitable for high-throughput expression screening applications" Nucleic Acids Res 2007, vol. 35, e45

Corchero J L, et al., "Integrated approach to produce a recombinant, his-tagged human alpha-galactosidase a in mammalian cells", Biotechnol Prog. 2011, vol. 27, pp. 1206-1217

Desnick R J, et al. "Fabry's disease: enzymatic diagnosis of hemizygotes and heterozygotes. Alpha-galactosidase activities in plasma, serum, urine, and leukocytes", J. Lab. Clin. Med. 1973, vol. 81, pp. 157-171

Mayes J S., et al. "Differential assay for lysosomal alpha-galactosidases in human tissues and its application to Fabry's disease" Clin. Chim. Acta 1981, vol. 112, pp. 247-251

Cano-Sarabia, M. et. al. "Preparation of Uniform Rich Cholesterol Unilamellar Nanovesicles Using CO2-Expanded Solvents". Langmuir 2008, vol. 24, pp. 2433-2437

Shu L., et al. "An in vitro model of Fabry disease" J. Am. Soc. Nephrol. 2005, vol. 16, pp. 2636-45

The invention claimed is:

1. A conjugate, comprising:
   i) a sterol;
   ii) a chain of polyethylene glycol having a proximal end and a distal end wherein said chain of polyethylene glycol is covalently bound by its proximal end to i) via an alkyl ether bond; and
   iii) a guiding ligand, capable of selectively binding to one or several receptors present in a target cell, said guiding ligand being covalently bound to the distal end of ii); wherein the guiding ligand is a peptide.

2. The conjugate of claim 1 wherein the sterol is cholesterol.

3. The conjugate of claim 1 wherein the chain of polyethylene glycol has a number of repetitions from 2 to 10.

4. The conjugate of claim 1 wherein the guiding ligand comprises an RGD sequence.

5. The conjugate of claim 4 wherein the guiding ligand is the peptide of sequence SEQ ID NO: 1.

6. A liposome comprising the conjugate of claim 1.

7. The liposome of claim 6, having a monomodal particle size distribution.

8. The liposome of claim 7 wherein the average particle size is from 25 up to 500 nanometers, and the average Z potential in absolute value is from 20 up to 90 mV.

9. The liposome of claim 6, further comprising a therapeutic agent.

10. The liposome of claim 9 wherein the therapeutic agent is α-galactosidase.

11. A method of delivering a therapeutic agent to a subject comprising administering the liposome of claim 9 to the subject.

12. A method of treatment comprising administering a therapeutically effective amount of the liposome of claim 9 together with pharmaceutically acceptable excipients or carriers, to a subject having Fabry disease.

13. A pharmaceutical composition comprising a therapeutically effective amount of the liposome of claim 9, together with pharmaceutically acceptable excipients and/or carriers.

14. A method for the preparation of the conjugate of claim 1 comprising the following steps:
   a) reacting a sterol with a sulfonyl halide in the presence of a base and a solvent to give the corresponding sulfonyl ester;
   b) reacting the compound obtained in the step a) with a polyethylene glycol with a number of repetitions from 2 to 10 in the presence of a solvent;
   c) activating the compound obtained in the step b) with disuccinimidyl carbonate; and
   d) reacting the compound resulting from the step c) with a peptide comprising the RGD sequence in the presence of a base and a solvent.

15. A method for the preparation of the liposome of claim 6 comprising the following steps:
   a) preparing an aqueous solution which may optionally include a surfactant;
   b) preparing a solution comprising:
      I) a conjugate, the conjugate comprising:
         i) a sterol;
         ii) a chain of polyethylene glycol having a proximal end and a distal end wherein said chain of polyethylene glycol is covalently bound by its proximal end to i) via an alkyl ether bond; and
         iii) a guiding ligand, capable of selectively binding to one or several receptors present in a target cell, said guiding ligand being covalently bound to the distal end of ii); and
      II) cholesterol and, optionally, a phospholipid dissolved in an organic solvent, where the organic solution is expanded with a compressed fluid;
   c) optionally, adding a therapeutic agent either to the solution of step a), or to the solution of the step b) before expanding this solution; and
   d) depressurizing the solution resulting from step b) over the resulting solution of step a).

16. A liposome comprising the conjugate of claim 4.

17. The liposome of claim 16, further comprising a therapeutic agent.

18. The liposome of claim 16, wherein the therapeutic agent is α-galactosidase.

19. A method of treatment comprising administering therapeutically effective amount of the liposome of claim 17, together with pharmaceutically acceptable excipients or carriers, to a subject having Fabry disease.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<221> NAME/KEY: SOURCE
<222> LOCATION: 1..5
<223> OTHER INFORMATION: /mol_type="protein"
      /note="RGD K are L-aminoacids, F is D-aminoacid"
      /organism="Artificial Sequence"

<400> SEQUENCE: 1

Arg Gly Asp Phe Lys
1               5
```